US00PP22044P2

(12) United States Plant Patent
Lemon

(10) Patent No.: US PP22,044 P2
(45) Date of Patent: Jul. 26, 2011

(54) GERANIUM PLANT NAMED 'OGLGER4090'

(50) Latin Name: *Pelargonium×hortorum*
Varietal Denomination: OGLGER4090

(75) Inventor: David G. Lemon, Lompoc, CA (US)

(73) Assignee: Ecke Geraniums, LLC, Encinitas, CA (US)

( * ) Notice: Subject to any disclaimer, the term of this patent is extended or adjusted under 35 U.S.C. 154(b) by 0 days.

(21) Appl. No.: 12/653,962

(22) Filed: Dec. 21, 2009

(51) Int. Cl.
*A01H 5/00* (2006.01)

(52) U.S. Cl. ..... Plt./329

(58) Field of Classification Search ..... Plt./329, Plt./328

See application file for complete search history.

(56) References Cited

OTHER PUBLICATIONS

Upov-rom Plant Variety Database 2010/06, Citation for *Pelargonium* 'Oglger4090' one page.*

* cited by examiner

*Primary Examiner* — June Hwu
(74) *Attorney, Agent, or Firm* — C. A. Whealy

(57) ABSTRACT

A new and distinct cultivar of Zonal Geranium plant named 'OGLGER4090', characterized by its upright, outwardly spreading and mounded plant habit; moderately vigorous growth habit; freely branching habit; freely flowering habit; medium green-colored leaves; light red purple-colored flowers; and good garden performance and high temperature tolerance.

1 Drawing Sheet

Botanical designation: *Pelargonium×hortorum*.
Cultivar denomination: 'OGLGER4090'.

BACKGROUND OF THE INVENTION

The present invention relates to a new and distinct cultivar of Zonal Geranium plant, botanically known as *Pelargonium×hortorum,* and hereinafter referred to by the name 'OGLGER4090'.

The new Zonal Geranium plant is a product of a planned breeding program conducted by the Inventor in Lompoc, Calif. The objective of the breeding program is to create new Zonal Geranium cultivars with attractive leaf and unique flower coloration.

The new Zonal Geranium plant originated from a cross-pollination made by the Inventor in March, 2003 in Lompoc, Calif. of *Pelargonium×hortorum* 'Pacwu', disclosed in U.S. Plant Pat. No. 16,171, as the female, or seed, parent with a proprietary selection of *Pelargonium×hortorum* identified as code number 9007, not patented, as the male, or pollen, parent. The new Zonal Geranium plant was discovered and selected by the Inventor as a single flowering plant from within the progeny of the stated cross-pollination in a controlled greenhouse environment in Lompoc, Calif. in March, 2004.

Asexual reproduction of the new Zonal Geranium plant by vegetative terminal cuttings in a controlled greenhouse environment in Connellsville, Pa. since April, 2005, has shown that the unique features of this new Zonal Geranium plant are stable and reproduced true to type in successive generations.

SUMMARY OF THE INVENTION

Plants of the new Zonal Geranium have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'OGLGER4090'. These characteristics in combination distinguish 'OGLGER4090' as a new and distinct cultivar of Zonal Geranium:

1. Upright, outwardly spreading and mounded plant habit.
2. Moderately vigorous growth habit.
3. Freely branching habit.
4. Freely flowering habit.
5. Medium green-colored leaves.
6. Light red purple-colored flowers.
7. Good garden performance and high temperature tolerance.

Plants of the new Zonal Geranium differ primarily from plants of the female parent, 'Pacwu', in flower color as plants of 'Pacwu' have light purple-colored flowers.

Plants of the new Zonal Geranium differ primarily from plants of the male parent selection in flower color as plants of the male parent selection have darker-colored flowers.

Plants of the new Zonal Geranium can be compared to plants of *Pelargonium×hortorum* 'Lilac Chiffon', disclosed in U.S. Plant Pat. No. 9,552. In side-by-side comparisons conducted in Lompoc, Calif., plants of the new Zonal Geranium differed primarily from plants of 'Lilac Chiffon' in the following characteristics:

1. Plants of the new Zonal Geranium had darker green-colored leaves than plants of 'Lilac Chiffon'.
2. Plants of the new Zonal Geranium and 'Lilac Chiffon' differed in flower color as plants of 'Lilac Chiffon' had lilac pink-colored flowers.

BRIEF DESCRIPTION OF THE PHOTOGRAPHS

The accompanying colored photographs illustrate the overall appearance of the new Zonal Geranium plant, showing the colors as true as it is reasonably possible to obtain in colored reproductions of this type. Colors in the photographs may differ slightly from the color values cited in the detailed botanical description which accurately describe the colors of the new Zonal Geranium plant.

The photograph at the bottom of the sheet comprises a side perspective view of a typical flowering plant of 'OGLGER4090' grown in a container.

The photograph at the top of the sheet is a close-up view of a typical inflorescence of 'OGLGER4090'.

DETAILED BOTANICAL DESCRIPTION

The aforementioned photographs and following observations, measurements and values describe plants grown in 10-cm containers in Encinitas, Calif. in a plastic-covered greenhouse during the spring and under conditions which closely approximate Zonal Geranium commercial production. During the production of the plants, day temperatures averaged 24° C., night temperatures averaged 16° C. and light levels averaged 4,000 foot-candles. Plants were 13 weeks old when the photographs and the description were taken. In the detailed description, color references are made to The Royal Horticultural Society Colour Chart, 2007 Edition, except where general terms of ordinary dictionary significance are used.

Botanical classification: *Pelargonium×hortorum* 'OGLGER4090'.

Parentage:

*Female, or seed, parent.*—*Pelargonium×hortorum* 'Pacwu', disclosed in U.S. Plant Pat. No. 16,171.

*Male or pollen parent.*—Proprietary selection of *Pelargonium×hortorum* identified as code number 9007, not patented.

Propagation:

*Type.*—By vegetative terminal cuttings.

*Time to initiate roots, summer.*—About ten days at temperatures of 20° C.

*Time to initiate roots, winter.*—About two weeks at temperatures of 16° C.

*Time to produce a rooted young plant, summer.*—About four weeks at temperatures of 20° C.

*Time to produce a rooted young plant, winter.*—About four weeks at temperatures of 16° C.

*Root description.*—Medium in thickness, fleshy; white in color.

*Rooting habit.*—Moderate branching; moderately dense.

Plant description:

*General appearance.*—Upright, outwardly spreading and mounding plant habit; densely foliated.

*Growth and branching habit.*—Moderately vigorous; freely branching habit; about six primary lateral branches develop per plant.

*Plant height, to top of foliar plane.*—About 12 cm.

*Plant height, to top of umbels.*—About 18 cm.

*Plant diameter* (*spread*).—About 22 cm.

*Lateral branches.*—Length: About 5.8 cm. Diameter: About 6 mm. Internode length: About 6 mm. Texture: Pubescent to pilose. Strength: Strong; thick, tough. Color: Close to 146C.

Foliage description:

*Arrangement.*—Alternate; simple.

*Length.*—About 5.7 cm.

*Width.*—About 6.7 cm.

*Shape.*—Reniform.

*Apex.*—Rounded.

*Base.*—Cordate.

*Margin.*—Crenate and sinuate.

*Texture, upper and lower surfaces.*—Densely pubescent.

*Venation pattern.*—Palmate.

*Color.*—Developing leaves, upper surface: Close to 137A. Developing leaves, lower surface: Close to 137C. Fully expanded leaves, upper surface: Close to 137A; venation, close to 137C. Fully expanded leaves, lower surface: Close to 147B; venation, close to 147C. Zonation pattern: Width: About 2.1 cm. Distance, center of zone to margin: About 2.1 cm. Color: Close to 147A.

*Petiole.*—Length: About 6.5 cm. Diameter: About 2.5 mm. Texture, upper and lower surfaces: Smooth, glabrous. Color, upper and lower surfaces: Close to 146B.

Flower description:

*Flower arrangement.*—Rotate flowers arranged in hemispherical umbels arising from apical leaf axils; umbels displayed above the foliar plane on strong peduncles; flowers face upright to outwardly; flowers slightly cupped becoming flatter with development.

*Fragrance.*—None detected.

*Quantity of flowers.*—Freely flowering habit; about 30 flowers per umbel; about five umbels per plant at one time.

*Flowering season.*—In Encinitas, Calif., flowering is continuous during the spring and summer; plants begin flowering about twelve weeks after planting.

*Flower longevity.*—Individual flowers last about four to five days on the plant; flowers persistent.

*Umbel height.*—About 5.7 cm.

*Umbel diameter.*—About 9 cm.

*Flower diameter.*—About 4.3 cm.

*Flower depth* (*height*).—About 1.8 cm.

*Flower buds.*—Length: About 1.7 cm. Diameter: About 1 cm. Shape: Ovoid. Color: Close to 76B to 76C.

*Petals.*—Quantity per flower: About six in a single whorl. Length: About 2.4 cm. Width: About 2.4 cm. Shape: Roughly obovate. Apex: Rounded. Base: Attenuate. Margin: Entire. Texture, upper and lower surfaces: Smooth, glabrous; velvety. Color: When opening, upper surface: Close to N78B. When opening, lower surface: Close to N80D. Fully opened, upper surface: Close to N74B to N74C; towards the base, close to 76C; venation, close to N74B; color does not fade with development. Fully opened, lower surface: Close to N80D; at the base, close to NN155D; venation, close to N74B.

*Petaloids.*—Quantity per flower: About one or two. Length: About 1.3 cm. Width: About 4 mm. Shape: Irregular, mostly oblong. Apex: Rounded. Base: Attenuate. Margin: Mostly entire. Texture, upper and lower surfaces: Smooth, glabrous; velvety. Color: When opening and fully opened, upper surface: Close to N74C; towards the base, close to NN155D; venation, close to N74B; color does not fade with development. When opened and fully opened, lower surface: Close to N74D; at the base, close to NN155D; venation, close to N74D.

*Sepals.*—Quantity per flower: About five arranged in a single whorl. Length: About 1.3 cm. Width: About 2.5 mm. Shape: Narrowly elliptical. Apex: Acuminate. Base: Attenuate. Margin: Entire. Texture, upper surface: Smooth, glabrous. Texture, lower surface: Pubescent. Color, upper and lower surfaces: Close to 146C.

*Peduncle* (*umbel stem*).—Length: About 13.4 cm. Diameter: About 3.5 mm. Strength: Strong. Angle: About 30° to 45° from vertical. Texture: Pubescent. Color: Close to 146C.

*Pedicel* (*individual flower stem*).—Length: About 2.9 cm. Diameter: About 1.5 mm. Strength: Strong. Texture: Pubescent. Color: Close to 146D tinted with close to 178B.

*Reproductive organs*.—Androecium: Stamen quantity per flower: About nine or ten. Anther length: About 1 mm. Anther shape: Oblong. Anther color: Close to 174C. Pollen amount: Scarce. Pollen color: Close to 175B. Gynoecium: Pistil quantity per flower: One. Pistil length: About 8 mm. Stigma shape: Split into five parts, star-shaped. Stigma color: Close to 71A. Style length: About 3 mm. Style color: Close to 71A. Ovary color: Close to 138B.

*Seed/fruit*.—Seed and fruit development have not been observed.

Disease/pest resistance: Plants of the new Zonal Geranium have not been observed to be resistant to pathogens and pests common to Zonal Geraniums.

Garden performance: Plants of the new Zonal Geranium have been observed to tolerate rain, wind, and temperatures ranging from about 2° C. to about 35° C. and have demonstrated good garden performance.

It is claimed:

1. A new and distinct Zonal Geranium plant named 'OGLGER4090' as illustrated and described.

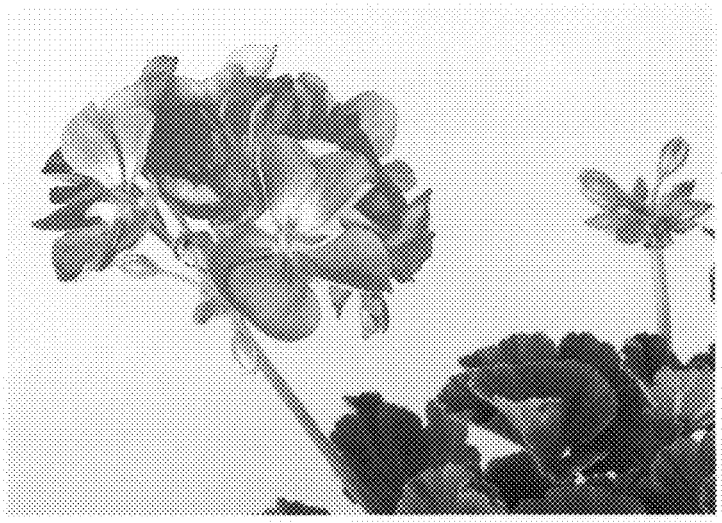
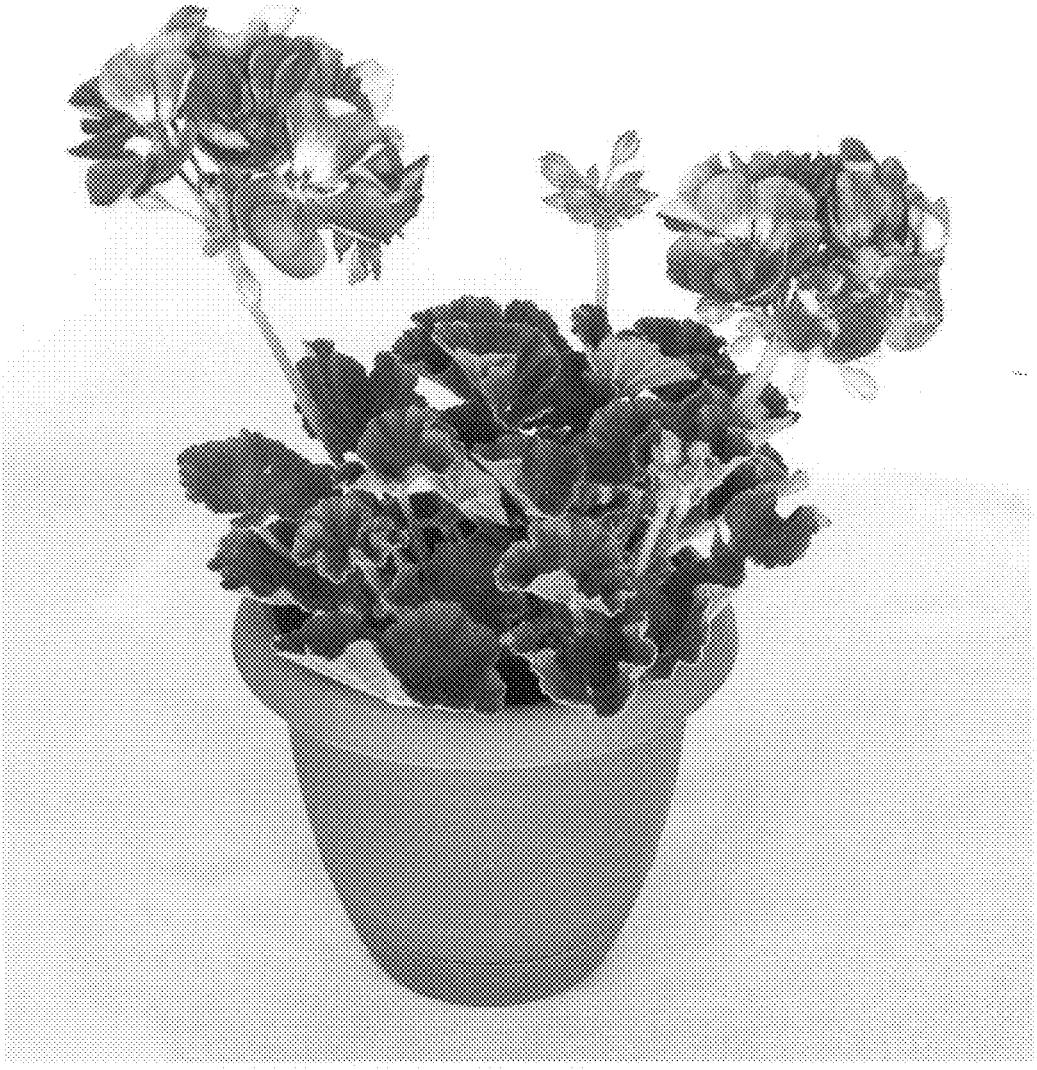

* * * * *